(12) United States Patent
Sampas et al.

(10) Patent No.: US 8,570,518 B2
(45) Date of Patent: Oct. 29, 2013

(54) METHODS AND MATERIALS FOR DETECTION OF TARGET SPECIES

(75) Inventors: Nicholas M. Sampas, San Jose, CA (US); Rene P. Helbing, Palo Alto, CA (US); Bo U. Curry, Redwood City, CA (US); Julie E. Fouquet, Portola Valley, CA (US); Carol T. Schembri, San Mateo, CA (US)

(73) Assignee: Alverix, Inc., San Jose, CA (US)

( * ) Notice: Subject to any disclaimer, the term of this patent is extended or adjusted under 35 U.S.C. 154(b) by 0 days.

(21) Appl. No.: 11/701,292

(22) Filed: Jan. 31, 2007

(65) Prior Publication Data

US 2008/0180673 A1    Jul. 31, 2008

(51) Int. Cl.
*G01N 21/00*    (2006.01)

(52) U.S. Cl.
USPC .......................................................... 356/432

(58) Field of Classification Search
USPC ......................................... 356/432, 439–442
See application file for complete search history.

(56) References Cited

U.S. PATENT DOCUMENTS

| 4,810,658 | A | * | 3/1989 | Shanks et al. ................. 436/172 |
| 5,745,231 | A | * | 4/1998 | Groger et al. ................. 356/128 |
| 6,850,328 | B1 | * | 2/2005 | Leirfall ......................... 356/432 |
| 7,349,080 | B2 | * | 3/2008 | Aklian .......................... 356/128 |
| 2002/0076729 | A1 | * | 6/2002 | Meyer et al. ................... 435/7.2 |
| 2004/0142494 | A1 | * | 7/2004 | Sheppard et al. ............. 436/518 |

FOREIGN PATENT DOCUMENTS

WO    WO2005/103652    * 11/2005

* cited by examiner

*Primary Examiner* — Tara S Pajoohi Gomez
(74) *Attorney, Agent, or Firm* — K&L Gates LLP

(57) ABSTRACT

A test system includes an optical medium, a binding agent capable of capturing a target complex, and a light detector. The optical medium provides a light path, and the binding agent is positioned to hold the target complex in an evanescent field created by propagation of light along the light path. The complex interacts with the evanescent field and emits light that the detector positioned to detect. The optical medium and the detector can be included in an optical integrated circuit where detected light passes through the optical medium transverse to the direction of the light path.

14 Claims, 1 Drawing Sheet

METHODS AND MATERIALS FOR DETECTION OF TARGET SPECIES

BACKGROUND

Diagnostic test kits have been developed for detection or analysis of target biological and environmental species in samples. Such test kits provide convenience since they may be used at a point of care such as a home, a medical facility, or elsewhere. For example, in a work place, a drug test kit can be used to detect one or more specific drugs or drug metabolites in a sample from an employee, a potential employee, or any other person that has agreed to be tested. Diseases, blood chemistry, DNA sequencing, and conditions such as pregnancy can similarly be quickly and conveniently detected using diagnostic test kits at home or wherever the test is desired.

Many diagnostic tests employ binding assay techniques. In a typical binding assay, a liquid sample is introduced to a flow matrix, e.g., into a test strip, where a labeling substance such as an antibody with an attached dye or florescent material binds to the target species. The complex thus created then flows to an indicator region that is treated to capture and hold the specific complex containing the target species and the labeling substance. The presence of the target species can then be detected through a change in the properties in the indicator region. For example, an accumulation of dye causing the indicator region to change color marks the presences of the target species in the sample.

Human observation has traditionally been used to determine the test results indicated by the change or lack of change in indicators of a diagnostic test kit. However, automated or electronic test evaluation may more reliably provide results, and integrated test systems or ICs are sought to provide test results without requiring human judgment. Such test systems would ideally be efficient and low cost for economic use in the widest variety of test situations.

SUMMARY

In accordance with an aspect of the invention, a test system can detect the presence of a target species in a sample from light emitted in a direction transverse to the direction of input radiation. The test system can be integrated into a compact and low cost configuration.

One specific embodiment of the invention includes a light guide and a binding agent positioned to trap a target species or complex in an evanescent field of the light guide. The target species or complex when present interacts with the evanescent field of light propagating through a waveguide and emits light in a direction transverse to the waveguide, for example, by fluorescence or scattering. A detector positioned to detect the emissions transverse to the waveguide can generate a signal indicating a test result. The system can be integrated into an optical integrated circuit containing the waveguide and optionally the detector and a light source, and the binding agent can be coated on an exposed surface of the waveguide and exposed to the sample through a flow matrix.

BRIEF DESCRIPTION OF THE DRAWINGS

Use of the same reference symbols in different figures indicates similar or identical items.

DETAILED DESCRIPTION

Figure 1:
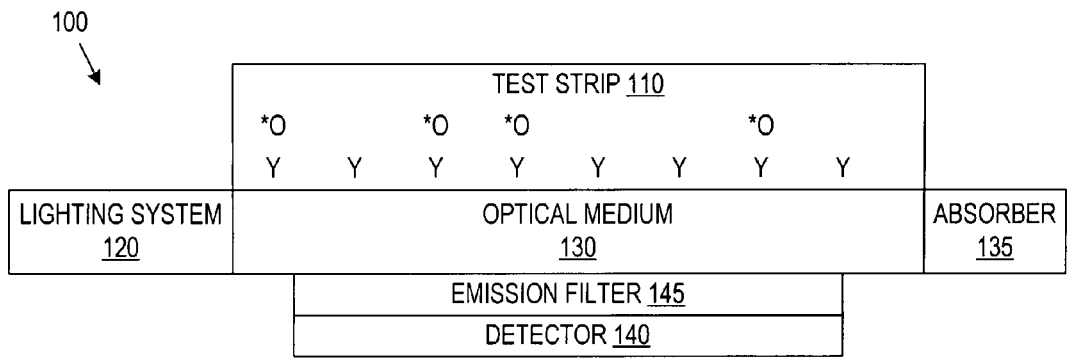
FIG. 1 shows an embodiment of a test system in accordance with an embodiment of the invention that detects emissions transverse to the direction of excitation radiation.

A compact configuration for a diagnostic test system can be achieved by detecting indicator emissions that are transverse to a direction of input excitation. FIG. 1 shows an exemplary embodiment of a test system 100. Test system 100 includes a test strip 110, lighting system 120, an optical medium 130, and a detector 140.

Test strip 110 can be of conventional design and may, for example, be made of a hydrophilic fibrous or matt material that provides a flow matrix for transport of a liquid sample by wicking. Test strip 110 also includes one or more labeling substances that are adapted or selected to enter the sample and attach to a target species to form a complex *O. Such labeling substances are well known and may include fluorescent molecules, fluorescent particles, or quantum dots.

Lighting system 120 introduces electromagnetic radiation (i.e., light) into optical medium 130. A suitable lighting system 120 can be implemented using an active light source such as a flash lamp, a light emitting diode (LED), a laser diode (e.g., a VCSEL) and/or passive optical elements such as reflectors, lenses, and diffractive elements that collect light and direct that light into optical medium 130. The electromagnetic radiation input from lighting system 120 includes radiation of an excitation wavelength chosen to excite the labeling substance or the complex *O including the labeling substance, causing the complex *O to fluoresce or otherwise emit light. To reduce background light at the emitted wavelength, lighting system 120 may employ a filter that blocks light having the emitted wavelength while transmitting light having other wavelengths including the excitation wavelength. As described further below, while optical medium 130 controls propagation of light so that light from lighting system 120 propagates only in a plane of optical medium 130, emissions from the excited complex *O can be in any direction including transverse to the plane of the excitation radiation.

Optical medium 130 can be any medium capable of guiding the light from lighting system 120. Some examples of structures suitable for optical medium 130 include but are not limited to an optical light pipe, a thin polymer substrate, or a waveguide that may have a serpentine pattern extending under all or a portion of the area of test strip 110. Such optical mediums generally include cladding or variations in refractive index that prevent light from escaping the optical medium. However, a well known property of electromagnetic propagation in a waveguide or similar medium is the presence of an evanescent field that extends outside the waveguide. The strength of the evanescent field generally falls exponentially with distance from the interface and depends on the refractive indices of the waveguide and its surroundings. Optical medium 130 is such that the light propagating through optical medium 130 produces such an evanescent field that extends a sufficient distance from the interface to provide a coupling with any of the labeling substance found close to optical medium 130.

At the interface of test strip 110 and optical medium 120 are binding agents Y. Binding agents Y may be or contain ligands, antibodies, antigens, proteins, nucleic acid, or other material that is selected to capture and hold the target species or the complex *O including the target species and a labeling substance. Binding agents Y can be coated on optical medium 120, part of test strip 110, or otherwise held at a position such that any of the target species or complex *O that binding agent Y captures are held within the evanescent field around optical medium 130.

The target species or complex *O as noted above is of a type that interacts with the evanescent field just outside optical medium 130 and then emits at least some light in a direction transverse to optical medium 130. In an exemplary embodiment of the invention, the target species or complex *O is fluorescent or contains a quantum dot or similar structure that absorbs energy from the evanescent field around optical medium 120 and then emits light or radiation in random directions. Transversely emitted radiation can pass through optical medium 130 and reach detector 140. If desired, a reflector (not shown) can be provided in or above test strip 110 to reflect light emitted in a direction away from optical medium 130 back through optical medium 130 to be read by detector 140.

The input radiation is normally confined to optical medium 130 and an absorber 135 can be provided at the end or edges of optical medium 130 to avoid stray reflection that might reach detector 140, causing noise. However, with a fluorescent label or quantum dot, a test operation can direct excitation radiation through the optical medium 130 for a limited time and then observe the transverse radiation emitted after the excitation radiation is shut off. This technique can reduce the background or noise signal that might otherwise result from stray reflections or leakage from optical medium 120 while the excitation radiation propagates through optical medium 120. Alternatively, light emitted from the target complex *O while the excitation radiation is on may provide a measurable signal, so that a label that fluoresces with long decay time is not required, and a target complex *O that merely scatters light from the evanescent field may be also be suitable.

Detector 140 is a general light detector suitable for detecting the frequency of light emitted from the target complex *O and, for example, may be a PIN photodiode, an avalanche photodiode, an amorphous silicon detector, or a detector array, such as a CCD array or CMOS sensor. Additionally, an emission filter 145 can be employed to reduce signal noise by blocking wavelengths that differ from the wavelength of light emitted from the target complex *O. Emission filter 145 can be, for example, an optical band pass filter or long pass filter with wavelength parameters selected according to the properties of the target complex *O. Conventional optical filter types such as absorbing filters or interference filters can be used for emission filter 145, but an interference filter may require collimation of the input light, which a micro-channel plate (not shown) between emission filter 145 and binding agents Y might provide.

Test system 100 can be implemented using discrete or integrated components and may be packaged in a test kit including the elements shown in FIG. 1 and perhaps a power source and/or a results display or printer. In one embodiment, each of test strip 110, lighting system 120, optical medium 130, and detector 140 are separately fabricated and then assembled to form test system 100. Alternatively, two or more of the components 110, 120, 130, and 140 can be fabricated as part of an integrated structure.

Figure 2:
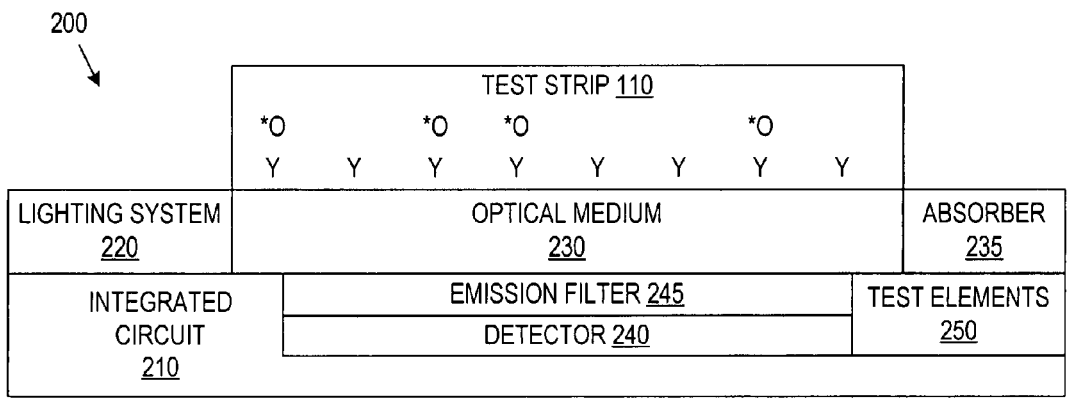
FIG. 2 shows a test system in accordance with an embodiment of the invention in which a lighting system, a waveguide, and a detector are integral parts of an optical integrated circuit that detects transverse emissions.

FIG. 2 illustrates an embodiment of a test system 200 including an optical integrated circuit 210 that incorporates a lighting system 220, an optical medium 230, an absorber 235, a detector 240, and an emission filter 245. Lighting system 220, optical medium 230, absorber 235, detector 240 and emission filter 245 perform substantially the same functions and may have substantially the same structure as described above respectively for lighting system 120, optical medium 130, absorber 135, detector 140 and emission filter 145. However, in test system 200, lighting system 220 and detector 240 are specifically electronic devices that are fabricated in a substrate and overlying layers of an integrated semiconductor structure. Additional electronic test elements 250 can also be fabricated in integrated circuit 210 using know integrated circuit processing techniques. Such elements 250 may include but are not limited to control circuits for activation and use of test system 200, signal processing circuits that evaluate electrical signals from detector 240 to determine a test result, light emitting diodes (LEDs) and/or driver circuits for displays or printers providing visual or printed indications of test results, or interface circuits for signal I/O including output of electrical signal indicating test results. Optical medium 230, absorber 235, emission filter 245 are optical elements that can be fabricated in or on the semiconductor structure using known techniques. The fabrication process for optical integrated circuit 210 leaves a surface of optical medium 230 available for a coating containing binding agents Y. Test strip 110 can then be attached to optical integrated circuit 210, and the system can be packaged as desired for convenient use.

Figure 3:
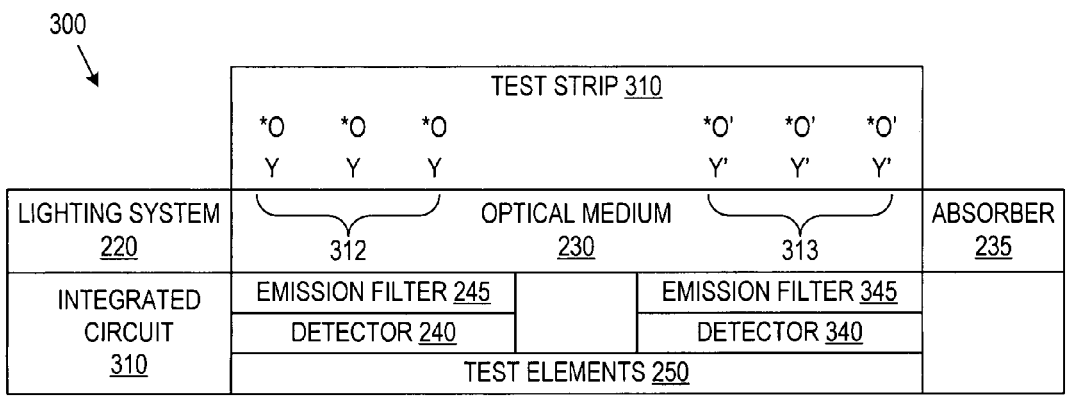
FIG. 3 shows a test system in accordance with an embodiment of the invention that detects transverse emissions from multiple indicator regions.

The exemplary embodiments of FIGS. 1 and 2 illustrate test systems capable of detecting a single target species. Alternative configurations can test simultaneously for multiple species. FIG. 3 shows an example of a test system 300 capable of simultaneously detecting multiple target species in a liquid sample. The multiplex geometry test system 300 is alternatively or additionally able to provide indicators for both positive and negative controls, which may be required for diagnostic assays. To test for two target species or positive and negative controls, test system 300 includes an optical integrated circuit 310 containing the same elements as described above for optical integrated circuit 210 of FIG. 2, except that optical integrated circuit 310 includes an additional light detector 340 and an associated emission filter 345 for detection of a second target species as described further below. To test for two target species, a test strip 310 contains two labeling substances that are adapted or selected to respectively attach to the two different target species to form two distinct complexes *O and *O'. Alternatively, a single labeling substance may be able to form one complex *O or *O' with one target species attached and a second complex *O' or *O if a different target species or no target species is attached (i.e., for a negative control.)

Two different binding agents Y and Y' are coated on separated indicator regions 312 and 313 on optical medium 230. The indicator region 312 containing one binding agent Y captures and holds one complex *O in the evanescent field adjacent optical medium 230, and the indicator 313 region containing the other binding agent Y' similarly captures and holds the other complex *O' in the evanescent field adjacent optical medium 230.

As illustrated in FIG. 3, indicator 312 and 313 regions are respectively positioned so that light emitted in a transverse direction from complex *O reaches detector 240 and light emitted in a transverse direction from complex *O' reaches detector 340. Independent electrical signals from detectors 240 and 340 can then respectively indicate the presence and/or quantity of respective complexes *O and *O'. To avoid cross-talk noise, indicator regions 312 and 313 can be laterally separated from each other and optical medium 230 may have a serpentine structure, baffles, or other light blocking structures to prevent light from indicator region 312 from reaching detector 340 and prevent light from indicator region 313 from reaching detector 240. Alternatively, indicator regions 312 and 313 may be on completely separate waveguides in optical medium 230. Baffles or separations may be alternatively or additionally be employed in lighting system 220 or between lighting system 220 and optical medium 230 to separate light beams. Emission filters 245 and 345 can also be used to distinguish targeted emitted light when complexes *O and *O' emit light of different frequencies.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A test system comprising:
   (a.) an optical medium providing a light path, wherein the optical medium has a first dimension and a second dimension that is smaller than the first dimension;
   (b.) a light source positioned adjacent to an end of the optical medium to introduce light directly into the second dimension of the optical medium such that the light emitted from the light source travels along the first dimension of the optical medium;
   (c.) a binding agent that captures a target complex, wherein the binding agent is positioned to hold the target complex in an evanescent field created by propagation of light along the light path; and
   (d.) a detector positioned transverse to the light path to detect light emitted from the target complex as a result of an interaction of the target complex with the evanescent field,
   wherein the binding agent is on a first side of the light path, and the detector is on a second side of the light path, the second side being opposite to the first side.

2. The system of claim 1, further comprising a lighting system positioned to introduce the light into the optical medium.

3. The system of claim 1, wherein the light source, the detector and the optical medium are integrated components of an optical integrated circuit.

4. The system of claim 3, wherein the optical integrated circuit further comprises a signal processing circuit that evaluates an electrical signal from the detector.

5. The system of claim 3, wherein the optical integrated circuit further comprises a light emitting diode to provide a visual indication of a test results.

6. The system of claim 3, wherein the optical integrated circuit further comprises an interface circuit to output an electrical signal indicating a test result.

7. The system of claim 1, further comprising a test strip having an interface with the optical medium, wherein the binding agent is at the interface of the test strip and the optical medium.

8. A test system comprising:
   (a.) an optical integrated circuit including a detector and an optical medium providing a light path overlying the detector, wherein the optical medium has a first dimension and a second dimension that is smaller than the first dimension;
   (b.) a light source positioned adjacent to an end of the optical medium to introduce light directly into the second dimension of the optical medium such that the light emitted from the light source travels along the first dimension of the optical medium; and
   (c.) a first binding agent overlying the optical medium, wherein the first binding agent holds a first target species in an evanescent field of light propagating in the optical medium; wherein the detector is positioned transverse to the light path to detect light emitted from the first target species that pass through the optical medium as a result from interaction of the first target species with the evanescent field, and wherein the binding agent is on a first side of the optical medium, and the detector is on a second side of the optical medium, the second side being opposite to the first side.

9. The system of claim 8, wherein the optical integrated circuit further comprises an absorber positioned to absorb light that passes through the optical medium.

10. The system of claim 8, wherein the optical integrated circuit further comprises a signal processing circuit that evaluates an electrical signal from the detector.

11. The system of claim 8, wherein the optical integrated circuit further comprises a light emitting diode to provide a visual indication of a test results.

12. The system of claim 8, wherein the optical integrated circuit further comprises an interface circuit to output an electrical signal indicating a test result.

13. The system of claim 8, further comprising:
   (a.) a second binding agent overlying the optical medium, wherein the second binding agent holds a second target species in an evanescent field of light propagating in the optical medium; and
   (b.) a second detector in the optical integrated circuit and underlying the optical medium, wherein the second detector is positioned to detect emitted light that passes through the optical medium as a result from interaction of the second target species with the evanescent field.

14. The system of claim 13, wherein the optical medium comprises:
   (a.) a first light path that passes under the first binding agent; and
   (b.) a second light path that passes under the second binding agent.

* * * * *